United States Patent [19]

Jain

[11] Patent Number: 5,731,418
[45] Date of Patent: Mar. 24, 1998

[54] COLLAGEN-BASED SORBENT POLYMER AND METHOD OF PREPARING SAME

[76] Inventor: Manoj J. Jain, 7420 Falcon St., Topeka, Kans. 66610

[21] Appl. No.: 691,444

[22] Filed: Aug. 2, 1996

Related U.S. Application Data

[63] Continuation of Ser. No. 376,643, Jan. 20, 1995, abandoned, which is a continuation of Ser. No. 224,405, Apr. 7, 1994, abandoned, which is a continuation of Ser. No. 991,137, Dec. 16, 1992, abandoned.

[51] Int. Cl.$^6$ .............................. B01J 20/26; C07K 1/14; C07K 14/78
[52] U.S. Cl. .............................. 530/356; 502/403; 530/427
[58] Field of Search .............................. 502/403; 428/402; 530/356, 427

[56] References Cited

U.S. PATENT DOCUMENTS

| | | | |
|---|---|---|---|
| 3,632,361 | 1/1972 | Battista | 530/356 |
| 4,483,829 | 11/1984 | Guardini | 530/343 |
| 5,024,841 | 6/1991 | Chu et al. | 530/356 |
| 5,153,067 | 10/1992 | Yoshida et al. | 428/402 |
| 5,162,506 | 11/1992 | Hadden | 530/427 |

OTHER PUBLICATIONS

Pulse Drying Systems, Inc. Brochure; 1989.
Sinnamun et al.; ALCA News, 1971, p. 235.
Whitmore, et al.; Preparation of Hide Collagen for Food, pp. 382–389.
Turkot et al., Food Technology, Apr. 1978, pp. 48–57
Sonodyne Industries, Inc. Brochure; Chemical Engineering, Jan. 10, 1983.
Huc et al.; JALCA, vol. 80, 1985, pp. 195–213.
Lipsett; The Roit Corporation; Abstract; Offal Blue BioCore Brochure.
Lindhahl; Sonodyne Industries; 20th Annual Conference, Oct. 1980, International Association of Fish Meal Manufacturers; Athens, Greece, pp. 1–5.
Komanowsky et al.; Comminuted Collagen for Novel Applications; USDA, pp. 410–422; 1974; vol. LXIX, No. 9; Journal of American Leather Chemists Association.

*Primary Examiner*—Jeffrey E. Russel
*Attorney, Agent, or Firm*—Hovey, Williams, Timmons & Collins

[57] ABSTRACT

A modified collagen product adapted for use as a sorbent is provided which includes collagen polymer having a density of from about 0.2–1.3 g/ml, an intrafibril pore size of from about 25–150 microns, and up to about 80% of the helicity of otherwise identical, unmodified naturally occurring polymer. The product is advantageously formed using leather scraps derived from tanning operations. The method for producing the collagen product of the invention includes first providing wet, detanned, leather-derived collagen and flash drying this material to remove substantial moisture therefrom while preventing the temperature of the detanned material from rising above about 130° F. This process permits substantial drying without undesired chemical modification of the collagen.

18 Claims, 1 Drawing Sheet

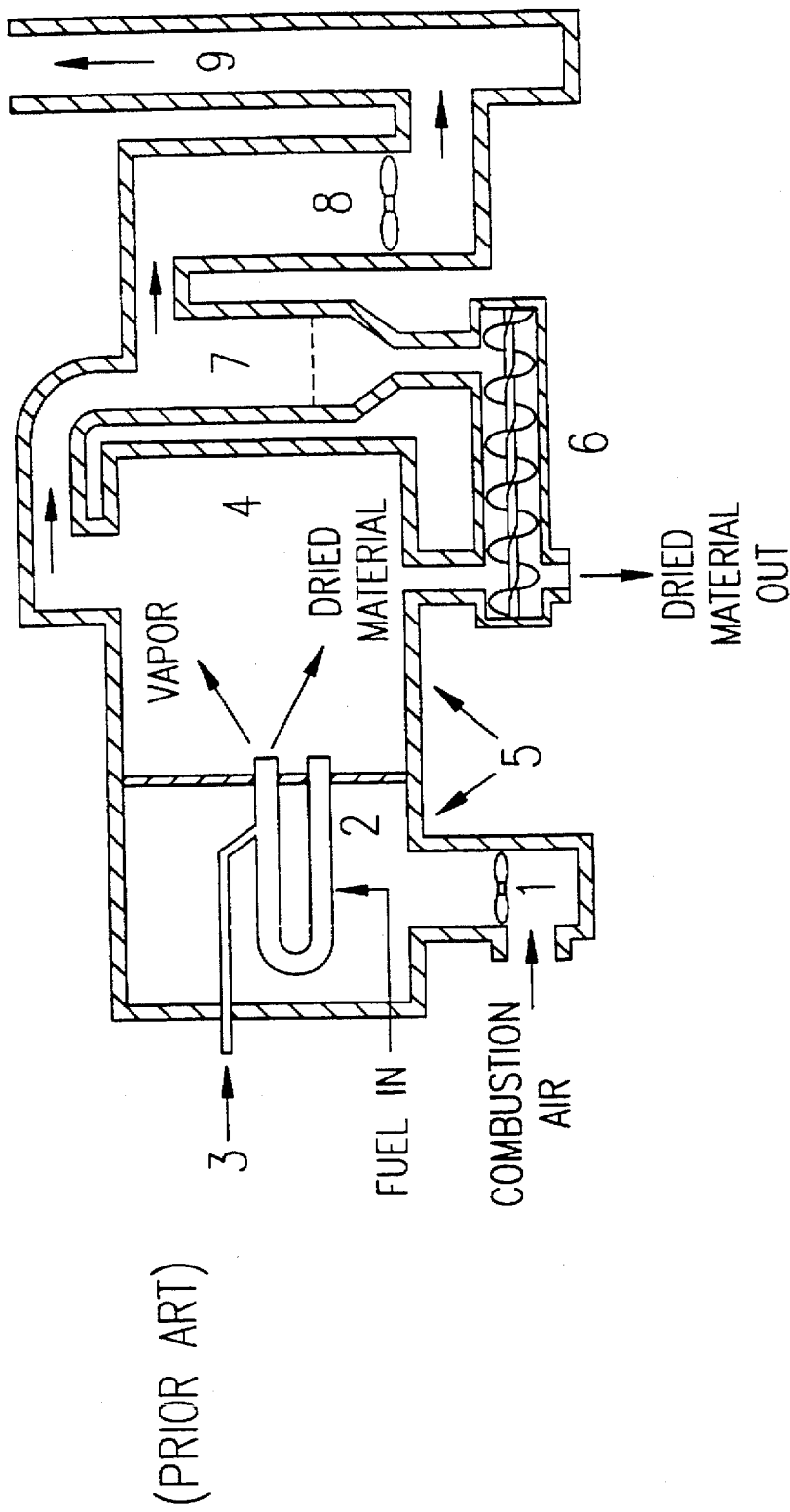

COLLAGEN-BASED SORBENT POLYMER AND METHOD OF PREPARING SAME

This application is a continuation of application Ser. No. 08/376,643, filed Jan. 20, 1995, now abandoned, which is a continuation of 08/224,405, filed Apr. 7, 1994, now abandoned, which is a continuation of Ser. No. 07/991,137, filed Dec. 16, 1992, now abandoned.

BACKGROUND OF THE INVENTION

1. Field of the Invention

The present invention is broadly concerned with a low-cost modified collagen product, as well as a method of producing the same, wherein the product has special utility as a sorbent for a wide variety of water and oil-based liquids. More particularly, it is concerned with such a modified collagen product which is preferably produced from leather scraps which have heretofore presented disposal problems, wherein the leather scraps are first detanned and then subjected to flash drying so as to remove moisture from the leather-derived collagen without significantly raising the temperature thereof; in this way, up to about 80% of the helicity of the collagen is preserved, and the sorbent qualities of the collagen are maintained.

2. Description of the Prior Art

Collagen is a naturally occurring protein polymer found in the connective tissues and hides of animals. As a natural polymer, collagen has many useful characteristics, including biodegradability, stability, strength, the ability to be transformed into various shapes and forms, incinerability, and the lack of toxic and hazardous characteristics. Collagen has been used in medical products such as sterile absorptive sponges and as a part of skin and bone substitutes.

Although a total of 12 collagen varieties have been identified, type I collagen is the most abundant form and is available from many sources including bovine hides. This collagen in nature consists of three alpha chains with a repeating GLY-X-Y sequence where X and Y are often proline and hydroxyproline respectively staggered by one amino acid relative to one another. The presence of these amino acids gives type I collagen its structural rigidity. Each individual polymer chain exists as a left-handed helix and has a molecular weight of approximately 100,000. These left-handed helices intertwine giving rise to a right-handed super helix with an axial rise of approximately 39 residues and a molecular weight of approximately 285,000. The super helix is stabilized by inter- and intramolecular interactions between side chains and by hydrogen bonded water bridges. The collagen molecule has characteristic dimensions of 300 nm×1.5 nm. There also exists in this collagen form two non-helical regions, termed the carboxy and amino terminals and sometimes referred to as telopeptides. These are important in crosslinking and self-assembly of type I collagen. Aggregation of collagen molecules results in the formation of collagen fibrils which in turn give rise of collagen fibers. The ability to self-assembly is directly related to the amino acids sequence found in naturally occurring collagen. When polymerized, a characteristic banding pattern exists every 6.9 nm which lends strength and resilience to the collagen fibers. The usefulness of collagen in medical devices is thus primarily a consequence of the ability of collagen to aggregate in vitro into various strong structures.

The nature and placement of side chains on the collagen polymers gives collagen its unique surface characteristics and contributes to its rigidity. These external "bristle" units may consist of carboxyl, sulfhydryl, and various amino acid groups. The net surface charge of naturally occurring collagen is generally positive due to these side chain groups, but can be altered through chemical modification.

The production of medical devices using collagen has typically involved purification of naturally occurring animal collagen to remove substantially all gelatin (to a level of less than 1% by weight), with subsequent freeze-drying and crosslinking or other chemical modifications. Freeze-drying substantially alters the characteristics of the naturally occurring collagen, and the resultant freeze-dried products have densities of 1.32 g/ml and above, as well as intrafibril pore sizes of from about 200–400 microns. As can be appreciated, techniques employed in the processing of naturally occurring collagen to yield medical devices are very expensive, and unsuited for mass production of collagen for other uses.

Animal skins consist mainly of collagen with certain impurities, most notably gelatin. In the process of making leather, hides are first tanned according to long-standing procedures using chromium compounds. In the final stages of leather production, the tanner shaves the hides to make a flat uniform leather surface. The resultant leather shavings are therefore inherently impure and contain significant quantities of the tanning agents and particularly chromium. Such leather shavings at present have no commercial value whatsoever, and are disposed of in landfills. This creates an environmental hazard, and also an economic burden to the tanner arising from shipping and landfill costs, as well as chemical loss. Furthermore, soon-to-be implemented environmental regulations will classify such leather scraps as a hazardous material, and this will greatly increase the disposal costs to tanners.

A number of sorptive materials have been developed and used in the past for the sorption of liquid materials such as aqueous or oil-based substances. The most efficient sorbents are the so-called super absorbent polymers, which are synthetic organic crosslinked species of low ionic strength which owe their sorbency to carboxylic groups protruding from the spine of the polymer. When an aqueous solution makes contact with such a polymer, the carboxyl groups solvate through hydrogen bonding, thereby sorbing the solution. While these super absorbent polymers are very effective, they are very costly and therefore cannot be used for the sorption of large spills.

There is accordingly a need in the art for novel modified collagen products having high sorbent capacities which can be produced at low cost from otherwise environmentally hazardous materials such as leather scraps, in order to provide an economical alternative to the use of super absorbent polymer products.

SUMMARY OF THE INVENTION

The present invention overcomes the problems outlined above, and provides a modified collagen product comprising collagen polymer which has been treated by flash drying in order to yield a highly sorbent, low-cost product. The modified product of the invention is preferably derived from leather scraps so that the invention not only provides a useful sorbent, but also eliminates a very significant waste disposal problem.

Broadly speaking, the modified collagen product of the invention comprises collagen polymer having an intrafibril pore size of from about 25–150 microns while exhibiting up to about 80% of the helicity of otherwise identical, unmodified naturally occurring collagen polymer. The modified product also has a density of from about 0.2–1.3 g/ml and includes from about 2–40%, and more preferably from about 2–20%, by weight of gelatin mixed with the collagen polymer.

In more detail, the preferred product has an intrafibril pore size of from about 50–100 microns and a preferred density of from about 0.6 to 1.0 g/ml. The collagen polymer should also have from about 60–80% of the helicity of otherwise identical, unmodified naturally occurring collagen polymer, and from about 2–40% by weight of naturally occurring gelatin mixed therewith. The most preferred collagen is type I collagen.

On a molecular level, the modified collagen polymer of the invention is in the form of left-handed helices each having an average molecular weight of from about 80,000–120,000 DA; these helices likewise form right-handed super helices having an average molecular weight of from about 240,000–330,000 DA.

The modified collagen products of the invention can exist in a wide variety of physical forms such as particles, scraps or sheets. In preferred forms, the product is in particulate, flowable form and has an average particle size of from about 75 microns to 1 mm. The products hereof should have the ability to absorb from about 40–65 times its weight of water, and the ability to absorb from about 10–20 times its weight or crude oil.

The method of the invention involves first providing a quantity of wet, detanned, leather-derived collagen which is substantially free (preferably less than about 5 ppm) of chromium. This wet material is then flash dried to remove moisture therefrom while preventing the temperature of the material from rising above about 130° F. Such drying may be accomplished by fluidized bed or vacuum drying, but most preferably is carried out by pulse-drying. In preferred forms of the inventions the flash drying is carried out while preventing the temperature of the material from rising above about 115° F.; generally speaking, this may be accomplished by contacting the wet material with heated air having a temperature of from about 1,000°–2,500° F. for a period of from about 1 millisecond to 0.5 second. More preferably, the contact time should be from about 0.25–0.4 seconds, and the air temperature (particularly where pulse-drying is used) should be from about 1,400°–1,800° F. The final moisture content of the dried material should be up to about 10% by weight, and more preferably from bone dry to 25% by weight.

BRIEF DESCRIPTION OF THE DRAWING

The single FIGURE is a schematic depiction of the type of pulse drying equipment preferred for use in the invention.

DETAILED DESCRIPTION OF THE INVENTION

The modified collagen product of the invention is most preferably obtained by starting with tanned leather scraps and shavings which can be obtained at little or no cost from any commercial tanning operation. These scraps must first be detanned by following a procedure heretofore used in the art for detanning of finished leather pieces.

By way of example, consider a one kilogram quantity of leather scraps and shavings exhibiting a characteristic greenish chrome color with an approximate moisture content of about 80% by weight. In the first detanning step, the 1 kilogram of scraps are contacted with 1–1.2 liters of an aqueous mixture of 0.8N NaOH and 10% NaCl, followed by mixing for about 30 minutes at ambient temperature. The mixture is then filtered and the liquid is brought back to strength by the addition of NaOH and NaCl. The scraps are then contacted with 1–1.2 liters of a second aqueous solution of 1.0N HCl and 5% NaCl, followed by 30 minutes mixing and filtering. The second solution is then brought back to strength as necessary and the scraps are subjected to repeated, identical contacting/filtering steps with the above described solutions until the scraps loose their characteristic greenish color.

The scraps are then repetitively contacted with solutions #3 and #4, namely an aqueous solution of 0.8N NaOH, 10% NaCl and 1% $H_2O_2$, and an aqueous solution of 1.0N HCl and 5% NaCl. In each respective step, 1–1.2 liters of solution are used, with 30 minutes mixing in each instance and intermediate filtering. The contacting with solutions #3 and #4 is carried out until the yellow color is removed from the scraps.

In the next stage, the treated scraps are contacted three successive times with 1–1.2 liters of solution #5, an aqueous solution of 0.8N NaOH, 10% NaCl and 1% $H_2O_2$, with 15 minutes mixing for each contacting step. The #5 wash solutions are filtered from the scraps and discarded.

The final step of the detanning process makes use of solution #6 which is a buffered solution containing citric acid and sodium citrate buffer (pH 4.8±0.2). Specifically, the shavings are washed three times with 1–1.2 liter quantities of solution #6 to remove traces of NaOH and $H_2O_2$. Thereafter, the shavings may be subjected to a final water wash. This results in white solid collagen shavings having substantially all of the chromium removed (≦5 ppm chromium).

After the detanning procedure is accomplished (and it will be understood that other equivalent techniques of detanning could be used if desired), the white shavings are flashed dried to remove moisture while preventing excess heating of the material. Such flash drying is most preferably carried out in a pulse dryer, such as a "Sono-Dri" pulse dryer commercialized by Sonodyne Industries, Inc. of Portland, Oreg. Such equipment is illustrated in the FIGURE which includes legends identifying the significant components thereof. The pulse combustor 2 is a generally U-shaped, valveless, aerodynamically designed burner having no moving parts which operates with a pulsating flame, with the shape of the burner controlling the firing rate. The combustor can use any liquid or gaseous fuel to produce drying heat at up to 2,500° F. and 250 cycles per second of sound energy. Energy output ranges from 3.2–3.5 MBTU/hr.

The pulse dryer makes use of the pulse combustor (lined with sound suppressive material 5) as its heat and energy source. As feed stock (here the detanned scraps) enter adjacent the upper outlet end of the combustor via feed 3, the sound shock waves created by the pulse combustor 2 break the cohesion between the water particles and the detanned solids. This increases the surface area of the water particles exposed to heat, thereby facilitating more efficient evaporation and drying. The rapid scrubbing away of surface water from the solids also aids in the outward migration of internal water for water evaporation. While the heat evaporates the water, sound oscillations continue to scrub the solids and keeps evaporated water from re-adhering to the scraps.

As described previously, the detanned scrap feed stock has a very short residence time in the drying section of the combustor (i.e., from about 1 millisecond to 0.5 second). About 80% of the water is removed in the pulse dryer/combustor itself, while the remaining 10% evaporates in the cyclone 4. This short residence time also assures that the temperature of the scraps is maintained at a relatively low level of no more than about 130° F. in the pulse dryer/combustor unit.

In more detail, the pulse drying process is initiated when air (via combustion air fan 1) and fuel are drawn into the lower leg of the U-shaped combustion chamber illustrated in the FIGURE and ignited by a spark. Hot gases created by the resulting detonation move in both directions from the combustion chamber. To the right as illustrated, the hot gases pass through an air inlet nozzle and air augmenter. To the left, the gases pass through the elbow and tailpipe pass the raw material injection area 3. Both streams of hot gases exhaust into a cylindrical collection vessel 4. An air augmenter is separated from the inlet nozzle by a few inches to allow an induced air draft be created by venting action of the gases exhausting at that point. The purpose of the air augmenter is to maintain proper temperature and air flows in the collection vessel 4.

Detonation in the combustion chamber causes the pressure therein to rise, momentarily shutting off the fuel supply which is maintained at a constant low pressure. It is this pressure fluctuation which causes the pulsing behavior of the combustor. The pressure fluctuation results in a very strong standing wave of sound energy. These waves, like the heat waves, move in both directions from the combustion chamber. The sound energy contained in these pressure waves is significant. The rate of pulsation is determined by the geometry of the combustor itself and does not require specific action on the part of the operator.

As the combustion chamber pressure falls between detonations, fuel is again admitted and mixed with air drawn through the inlet nozzle. Detonation occurs again because of contact between the explosive mixture and the spark or the sufficiently hot walls of the pulse chamber itself. Once the surface operating temperature of approximately 1,000° F. has been attained, the detonating spark can be extinguished and the process becomes self-igniting. The combustor will continue to pulse as long as it is supplied with fuel.

Repeated detonations create movements of hot gases within the hollow shell of the combustor engine. About 70% of the exhaust gases of the combustion cycle pass from the combustion chamber through the elbow and tailpipe section. The momentum of these gases leaves behind a temporary vacuum which draws more air into the combustion chamber for the next combustion cycle. The remaining 30% of the gases exit by reverse flow through the air inlet nozzle and the air augmenter.

Detonations occur at the rate of about 250 cycles per second, creating significant turbulence in the materials being dried. It is important to note that drying occurs between the raw material inlet 3 and the exhaust exit of the pulse chamber, a distance of less than 16 inches.

Raw material entering the drying zone of the pulse combustor is heavily laden with water. The sound waves produced by the combustor are used to break the bond between the solids and water. This atomizes the water into many fine droplets, creating increased surface area for evaporation. Also, the sound waves set in motion a scrubbing action that aids in the evaporative process. Heat present in the exhaust stream interacts with the atomized water, allowing highly efficient evaporation to occur. Theoretically, 1,150 BTU's are required to evaporate a pound of water. Typical drying efficiency is with equipment of the type depicted in the FIGURE are in the range of 1,400 to 1,500 BTU's per pound of water removed. During drying, evaporation of the water in the raw material absorbs most of the heat, and therefore leaves the material being dried in a relatively cool condition. Although operating conditions in the pulse combustor may exceed 2,500° F. (but are typically from about 1,000°–2,500° F.), residence time of the material in contact with the hot exhaust gases is very short, normally about 5 milliseconds, and typically ranging from about 1 millisecond–0.5 seconds.

The product leaving the auger 6 illustrated in the FIGURE may be ground or subdivided using any conventional technique. As indicated previously, the dried material should have a moisture content of up to about 10% by weight and a density of from about 0.2–1.3 g/ml.

The auger 6 is also connected to a dust handling system including an exhaust fan 8, dust collector 7 and spray tower 9; these components and the operation thereof are conventional.

The construction and operation of a pulse dryer of the type described herein and illustrated in the FIGURE is further explained in a paper distributed by the manufacturer and entitled "Basic Principles of Pulse Combustion Drying" by Thomas G. Lindahl; and also in a brochure entitled "Pulse Drying Systems, Inc.". This paper and the brochure are incorporated by reference herein.

A series of tests were conducted to measure the sorption efficiency of the dried collagen product in accordance with the invention. This product was prepared by detanning leather scraps according to the foregoing procedure, followed by flash drying and grinding to an average particle size of from about 0.1 mm to 1 mm. Sorption efficiency of the collagen material was tested using four liquids, namely distilled water, diesel fuel, gasoline and crude oil. The experiments were conducted according to the procedures outlined in ASTM F716-82 (reapproved 1986). Three runs were performed for each liquid and an average value was computed for absorption efficiency. The results obtained confirmed that the collagen swelled 54, 12.6, 8.7 and 13 times its dry weight when distilled water, diesel fuel, gasoline and crude oil were added to the collagen.

The results of these tests are briefly described below.

Distilled Water—Distilled water was added to the collagen product in a 100 cc glass cylinder and mixed by means of glass bar. Within two hours a column of swollen absorbent formed close to the top of the free water surface in the glass cylinder. The collagen absorbent swelled 54 times its dry weight.

Gasoline—After addition of gasoline and subsequent mixing of the collagen, the absorbent did not swell significantly. It was estimated that the swelling was 8.7 times the dry collagen weight.

Diesel—Collagen behavior in diesel was similar to the collagen behavior in gasoline. The average collagen absorbent swelling was 12.6 times the dry weight.

Crude Oil—Crude oil was added to the column of polymer in the glass cylinder and agitated using the glass bar. It was not possible to detect the height of the swollen collagen in the crude oil in order to obtain the weight of the swelled polymer. The content of the glass cylinder was carefully poured into a glass container which had a permeable filter in the bottom and placed at the top of 200 cc flask. The flask was connected to a vacuum and the oil was drained. The weight of the collagen left on the filter and the remaining polymer in the glass cylinder were used to compute the absorption efficiency. The material balance indicated that the collagen swelling in the oil was 13 times the original dry weight. However, the method used introduced some error due to loss of polymer through the permeable filter and the vacuuming effect on the swelled collagen.

It will therefore be seen that the collagen product of the invention can be used as a natural sorption "sponge" in a variety of contexts. For example, the product can be used to good effect for the cleanup of oil spills, especially for sweeping oil from the surface of water, both standing and flowing. Furthermore, the collagen can be used in lieu of expensive super absorbent synthetic polymers in virtually all applications where such materials are presently being employed.

I claim:

1. A modified collagen product comprising collagen polymer having an intrafibril pore size of from about 25–150 microns, said product having a density of from about 0.2 to 1.3 g/ml and further including from about 2–40% by weight of gelatin mixed with said collagen polymer, said product having the ability to absorb from about 40–65 times its weight of water, and the ability to absorb from about 10–20 times its weight of crude oil.

2. The product of claim 1, said intrafibril pore size being from about 50–100 microns.

3. The product of claim 1, said density being from about 0.6 to 1.0 g/ml.

4. The product of claim 1, said collagen polymer having from about 60–80% of the helicity of otherwise identical, unmodified naturally occurring collagen polymer.

5. The product of claim 1, said product being in the form of a particulate, flowable material having an average particle size of from about 75 microns to 1 mm.

6. The product of claim 1, said product having from about 2–20% by weight gelatin mixed with said collagen polymer.

7. The product of claim 1, said collagen polymer being type I collagen.

8. The product of claim 1, said collagen polymer being in the form of left-handed helices each having an average molecular weight of from about 80,000–110,000 DA.

9. The product of claim 1, said collagen polymer being derived from detanned leather.

10. A method of producing a modified collagen product comprising the steps of:

providing a quantity of wet, detanned, leather-derived collagen material which is substantially free of chromium; and flash drying said material to remove moisture therefrom while preventing the temperature of said material from rising above about 130° F., in order to produce said modified collagen product, said method being carried out so that the modified collagen product has an intrafibril pore size of from about 25–150 microns and a density of from about 0.2 to 1.3 g/ml and further including from about 2–40% by weight of gelatin mixed with collagen polymer, said product having the ability to absorb from about 40–65 times its weight of water, and the ability to absorb from about 10–20 times its weight of crude oil.

11. The method of claim 10, including the step of conducting said flash drying while preventing the temperature of said material from rising above about 115° F.

12. The method of claim 10, said flash drying including the step of contacting said material with heated air having a temperature of from about 1,000°–2,500° F. for a period of from about 1 millisecond to 0.5 second.

13. The method of claim 12, said flash drying being carried out by repeatedly contacting said material with pulses of said heated air such that the total contact time between said heated air and said material is from about 1 millisecond to 0.5 second.

14. The method of claim 12, said period being from about 0.25–0.4 seconds.

15. The method of claim 12, said air temperature being from about 1,400°–1,800° F.

16. The method of claim 10, said flash drying step being conducted such that the modified collagen product has a moisture content of up to about 25% by weight.

17. The method of claim 16, said moisture content being from about bone dry to 10% by weight.

18. The method of claim 10, said flash drying step being conducted such that the modified collagen product has up to about 80% of the helicity of otherwise identical, unmodified, naturally occurring collagen.

* * * * *